United States Patent
Boese et al.

(10) Patent No.: US 8,218,717 B2
(45) Date of Patent: Jul. 10, 2012

(54) RECONSTRUCTION OF 3D IMAGE DATASETS FROM X-RAY AND CONE-BEAM DATA

(75) Inventors: Jan Boese, Eckental (DE); Frank Dennerlein, Forchheim (DE); Holger Kunze, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/902,237

(22) Filed: Oct. 12, 2010

(65) Prior Publication Data

US 2011/0085637 A1     Apr. 14, 2011

(30) Foreign Application Priority Data

Oct. 12, 2009 (EP) .................................... 09012880

(51) Int. Cl.
*A61B 6/00* (2006.01)
(52) U.S. Cl. ............................................................ 378/4
(58) Field of Classification Search ................ 378/4, 15
See application file for complete search history.

(56) References Cited

U.S. PATENT DOCUMENTS

| | | | | |
|---|---|---|---|---|
| 6,292,525 | B1* | 9/2001 | Tam | 378/4 |
| 7,187,747 | B2* | 3/2007 | Bontus et al. | 378/15 |
| 7,280,632 | B2* | 10/2007 | Katsevich | 378/15 |
| 7,403,587 | B2* | 7/2008 | Bontus et al. | 378/4 |
| 7,477,720 | B2* | 1/2009 | Pack et al. | 378/4 |
| 7,822,171 | B2* | 10/2010 | Bontus et al. | 378/11 |
| 2003/0161444 | A1* | 8/2003 | Katsevich | 378/210 |
| 2005/0220265 | A1* | 10/2005 | Besson | 378/16 |
| 2006/0050842 | A1* | 3/2006 | Wang et al. | 378/16 |
| 2006/0067457 | A1* | 3/2006 | Zamyatin et al. | 378/4 |
| 2006/0109952 | A1* | 5/2006 | Chen | 378/4 |
| 2009/0207964 | A1* | 8/2009 | Pack | 378/4 |

OTHER PUBLICATIONS

Ye et al., Geometric studies on variable radius spiral cone-beam scanning, Med Phys, 31, Jun. 6, 2004, pp. 1473-1480.*
Yu et al., Katsevich-Type algorithms for variable radius spiral cone-beam, Developments in X-ray Tomography IV, Proc of SPIE, vol. 5535, 2004, pp. 550-557.*
Dennerlein et al., Cone-beam reconstruction from a variable-radius, planar source trajectory, IEEE Nuclear Science Symposium Conference Record, 2990, pp. 2496-2499.*
Dennerlein et al., "Cone-beam reconstruction from a variable-radius, planar source trajectory", 2009 IEEE Nuclear Science Symposium and Medical Imaging Conference (NSS/MIIC 2009), IEEE, Orlando, LL. USA, Oct. 24, 2009, pp. 2496-2499, XP031621443, ISBN: 978-1-4244-3961-4.

(Continued)

*Primary Examiner* — Edward Glick
*Assistant Examiner* — Alexander H Taningco

(57) ABSTRACT

A method for producing a 3D image dataset of an object with an imaging system having an x-ray source and an x-ray detector is provided. A series of two-dimensional arrays of cone beam data from the detector is acquired while the source moves along a substantially planar trajectory around the object. The trajectory is described by a series of source points serially numbered by a counter parameter. The cone beam data is differentiated with respect to the counter parameter at a fixed ray direction to produce a derivative of the cone beam data. The derivative is filtered with a Hilbert-like filter to produce filtered cone beam data. The acquired or the filtered cone beam data is multiplied with a redundancy weighting function. The cone beam data is back-projected to reconstruct a 3D image dataset.

14 Claims, 4 Drawing Sheets

OTHER PUBLICATIONS

Tang et al., "Analytical Image Reconstruction for Convergent-beam Non-circular Orbit Attenuation Correction", 9$^{th}$ International Meeting on Fully Three-Dimensional Image 2007 Reconstruction in Radiology and Nuclear Medicine, pp. 293-296, XP007912106.

Parker, "Optimal short scan convolution reconstruction for fan-beam CT", Med Phys, 9, (2), 1982, pp. 254-257.

Feldkamp et al., "Practical cone beam algorithm", J. Opt. Soc. Am. A1, 1984, pp. 612-619.

Noo et al., "A new scheme for view-dependent dta differentiation in fan-beam and cone-beam beam computed tomography", Phys. Med. Biol. 52, 2007, pp. 5393-5414.

\* cited by examiner

US 8,218,717 B2

RECONSTRUCTION OF 3D IMAGE DATASETS FROM X-RAY AND CONE-BEAM DATA

CROSS REFERENCE TO RELATED APPLICATIONS

This application claims priority of European application No. 09012880.2 filed Oct. 12, 2009, which is incorporated by reference herein in its entirety.

FIELD OF THE INVENTION

The invention relates generally to a method and an imaging system capable of producing a three-dimensional (3D) image dataset of an object. The imaging system comprises an X-ray source emitting X-rays in a cone-shaped beam (generally called cone beam) and a detector comprising a two-dimensional (2D) array of detector elements for acquiring one projection image (generally called cone-beam projection) of the object at a time. More particularly, the invention relates to a novel method for reconstructing a three-dimensional image data set from cone-beam data acquired by such imaging system.

BACKGROUND OF THE INVENTION

In fan-beam computed tomography (CT) systems, an X-ray source projects a fan-shaped beam which is collimated to lie within an xy-plane of a Cartesian coordinate system termed the imaging plane. The X-ray beam passes through the object being imaged, such as a medical patient, and impinges upon a one-dimensional array of radiation detectors. Each detector produces an electrical signal that is a measurement of the attenuation of the X-ray beam by the object. The source and detector array in a conventional CT-system are rotated on a gantry within the imaging plane around the object through an angle of 180-360°, wherein a set of views made at different angular orientations during one revolution of the X-ray source and detector are acquired. From the acquired attenuation data, it is possible to reconstruct a 2D-image of the xy-plane through the object. A common way of performing the image reconstruction in fan-beam CT is for example filtered backprojection.

Image reconstruction becomes mathematically more complex when the X-ray beam is cone-shaped and the detector accordingly is a 2D-array of detector elements. However, these geometries are generally used in interventional or angiographic X-ray systems, for example in C-arm-systems where the source and the detector are mounted on the ends of a C-shaped arm which is adapted to rotate around the patient. On the other hand, it is highly desirable to be able to obtain an three-dimensional image of a volume within the patient by rotating the C-arm once around the patient (One rotation around e.g. 180-360°, during which a set of X-ray projections is acquired, is called 3D scan). Therefore, 3D-image reconstruction from circular cone-beam data has been an active research field for the last decades. A practical solution for circular-based source trajectories is disclosed in L. A. Feldkamp, L. C. Davis and J. W. Cress, "Practical cone beam algorithm" J.Opt. Soc. Am. A1, 612-619 (1984). The Feldkamp method is an analytic reconstruction approach. Unfortunately, analytic reconstruction approaches have to be adapted to each novel acquisition geometry. In other words, the Feldkamp method cannot readily be used with a non-circular source trajectory.

Recently, X-ray systems having another acquisition geometry have become available, namely where the X-ray source and the detector are mounted on telescopic arms. However, these systems have not been used to reconstruct 3D images, because in such an X-Ray system, the X-ray source would move along a planar polygon-based trajectory during a 3D scan. Unfortunately, no reconstruction algorithm is available for cone beam projections obtained with a non-circular trajectory.

SUMMARY OF THE INVENTION

Thus, it is a problem of the present invention to provide an attractive analytic method for reconstructing a 3D image dataset from cone beam projections acquired along a planar, polygon-based X-ray source trajectory.

This object is met by the method, the imaging system and the computer program product according to the claims.

The claimed method allows to achieve CT-like reconstruction from X-ray projections acquired along a variable-radius, planar source trajectory. The claimed Feldkamp-like reconstruction algorithm yields exact results in the plane of the scan, in general approximate results within the rest of the 3D field-of-view (FOV) and also accurately recovers the shape of this FOV for a given geometry.

The two-dimensional array of detector elements is preferably arranged in a plane, thus resulting in a flat-panel detector.

During the acquisition, the X-ray source moves along a substantially planar trajectory around the object to be imaged, preferably a subject or patient. "Substantially planar" means that deviations from the plane due to constructional variability in the imaging system are allowed, as long as the reconstruction method still yields acceptable results. In practice, the trajectory may lie within about ±15 mm, preferably within about ±10 mm or ±8 mm from the central plane of the trajectory.

However, the main advantage of the present method is that the trajectory need not be circular, or indeed need not have any specific shape within that plane. Thus, it is a variable-radius trajectory, merely being described by a series of points in space (source points) serially numbered by a scalar $\lambda$, which is called counter parameter in the claims. The trajectory, in particular, may be none-convex, i.e. it may curve inwardly and outwardly. A convex trajectory could not curve outwardly with regard to the isocenter. In other words, the trajectory may have a non-convex shape, wherein the trajectory can be crossed by a line more than twice. $\lambda$ can in convex trajectories be thought of as the source polar angle, but this is not a requirement. Preferably, the distance between the source and the detector varies along the trajectory, wherein the variation is preferably significant, i.e. it is not an essentially circular trajectory with some tolerances, but the distance preferably varies by at least ±5 mm, preferably ±10 mm and most preferred by at least ±15 mm. In other words, the scan radius R, i.e. the distance between the source and the isocentre of the scan, is variable while the source moves around the object, i.e. along the trajectory. Again, the variation preferably is significant, i.e. by at least ±5 mm, preferably ±10 mm, wherein a non-circular scan radius is preferred. According to a preferred embodiment, at least part of the trajectory has the shape of a polygon, i.e. it is made-up of a finite number (preferably 2-30) straight lines.

While the source moves along the trajectory, a series of two-dimensional (2D) arrays of cone beam data are acquired by the detector. Each of these 2D arrays is a projection image of the object and in the following will also be called cone-beam (CB) projection. A series of CB projections acquired during one scan, i.e. one sweep of the source over the trajectory, are called cone beam data. As is usual for computed tomography, the trajectory should preferably span at least an angular scan interval around the object of 180° plus the cone beam angle, for example about 200°-300°.

The imaging system can be any X-ray system, but in particular can be one where X-ray source and detector are mounted on telescopic arms and/or rails and/or robotic arms or a combination thereof.

In the following, the reconstruction algorithm shall be described in detail, also in a mathematical description. However, it is to be noted that any other implementation of the method using the steps defined in claim 1 will also fall under the scope of the present patent application.

The trajectory along which the X-ray source moves during a scan can mathematically be written as $$\underline{a}(\lambda) = R(\lambda)(\cos \lambda, \sin \lambda, 0) \text{ with } \lambda \in \Lambda \quad (1)$$

The scalar $\lambda$ is the counter parameter of the points on the trajectory at which the cone beam projections are acquired and, as mentioned above, can be thought of as the source polar angle. $\Lambda$ can be thought of as the angular scan interval and $R(\lambda)$ describes the distance between the source and the origin (0, 0, 0) of the object coordinate system. This geometry is illustrated in FIG. 2. Thus, the parameter $\lambda$ is used to describe locations along the source trajectory. The detector 10 is preferably a flat-panel detector and u and v are the detector coordinates measured in horizontal and vertical direction, respectively. Thus, the detector is parallel to $\underline{e}_u(\lambda) = (-\sin \lambda, \cos \lambda, 0)$ and $\underline{e}_v(\lambda) = (0,0,1)$ and orthogonal to $\underline{e}_w(\lambda) = (\cos \lambda, \sin \lambda 0)$. The detector-source distance is allowed to vary smoothly during the scan and is denoted as $D(\lambda)$.

Although in FIG. 2, the plane of the detector is perpendicular to a line intersecting both of the origin of the object coordinate system and $\underline{a}(\lambda)$, this is not a requirement for the algorithm. The detector can also be tilted with regard to the central ray. Of course, it is preferable that it should not be tilted too much, since the field of view can only cover such areas of the object which are projected onto the detector.

The object 20 is represented by a circle in FIG. 2 and has an object density function $f(\underline{x})$.

The cone beam projections acquired by the detector 10 are denoted by the function $g(\lambda,u,v)$, such that the value $g(\lambda,u,v)$ corresponds to the object density integral along the line that connects the source position at $\underline{a}(\lambda)$ to the point $(u,v)$ on the corresponding detector. The unit direction of this line is noted in FIG. 2 with the vector $\underline{\alpha}$.

Mathematically the cone beam projections can be expressed as $$g(\lambda,u,v) = \int_0^\infty dt f(\underline{a}(\lambda) + t\underline{\alpha}(\lambda,u,v)) \quad (2)$$

where $u \in [-u_m, u_m]$ and $v \in [-v_m, v_m]$ are coordinates measured along $\underline{e}_u(\lambda)$ and $\underline{e}_v(\lambda)$ and where $$\underline{\alpha}(\lambda, u, v) = \frac{u\underline{e}_u(\lambda) + v\underline{e}_v(\lambda) - D(\lambda)\underline{e}_w(\lambda)}{\sqrt{u^2 + v^2 + D(\lambda)^2}} \quad (3)$$

In step A, a derivative of the cone beam data is calculated. Preferably, the data is differentiated with respect to the counter parameter of the source trajectory $\lambda$ at fixed ray direction $\underline{\alpha}$, for example using a differentiation scheme described in the article "A new scheme for view-dependent data differentiation in fan-beam and cone-beam computed tomography" by F. Noo, S. Hoppe, F. Dennerlein, G. Lauritsch and J. Hornegger, Phys. Med. Biol. 52 (2007) 5393-

5414. In an embodiment, the cone-beam data is differentiated with regard to all three spatial directions or angles, namely the view angle $\lambda$, the ray angle u in and the cone angle v (the vertical component). While u and v are not angles but the detector coordinates, they correspond to such angles. In other words, in this embodiment a full differentiation is made, also including the vertical component which is not relevant in fan-beam data, but only in cone-beam data. This has the effect that the differentiation (see formulae 5) has three terms.

Mathematically, the differentiation can be written as $$g_D(\lambda, u, v) = \frac{\partial}{\partial \mu} g(\mu, \underline{\alpha}(\lambda, u, v))\Big|_{\mu=\lambda} \quad (4)$$

if both, $|u| \leq u_m$ and $|v| \leq v_m$. If $|u| > u_m$ or $|v| > v_m$, however, we set $g_F(\lambda,u,v) = \circ$, where the symbol $\circ$ is used to define data outside the detector boundaries. We select $\circ$ to have the properties (i) $\circ + x = \circ$ and (ii) $\circ \cdot x = \circ$, so that it propagates through the computations and sets any point x in the reconstruction to $\circ$ that projects at least for one $\lambda \in \Lambda$ beyond the detector boundaries. Doing so, the algorithm automatically recovers the FOV, which takes in general non-trivial shapes in variable-radius geometries. In a practical implementation, $\circ$ can be set to the float value not a number (NaNq), which satisfies the requirements described above.

Equation (4) can be developed into $$g_D(\lambda, u, v) = \left( \begin{array}{l} \frac{\partial}{\partial \lambda} - \frac{uv}{D(\lambda)^2} \frac{\partial}{\partial v} + \\ \frac{D(\lambda)^2 + u^2}{D(\lambda)} \frac{\partial}{\partial u} + \\ \frac{u\left(\frac{\partial}{\partial \lambda}\right)D(\lambda)}{D(\lambda)} \frac{\partial}{\partial u} \end{array} \right) g(\lambda, \underline{\alpha}(\lambda, u, v)) \quad (5)$$

Compared to the corresponding equation in the circular geometry, this equation contains one additional term, namely the one in line 2 of (5), which we call NEW TERM and which will be investigated below.

After step A, the derivative of the cone-beam data is filtered with a Hilbert-like filter to produce filtered cone-beam data in a step B. The filtered cone-beam data may for example be given as $$g_F(\lambda, u, v) = \int_{-u_m}^{u_m} du' h_H(u - u') \frac{D(\lambda) g_D(\lambda, u', v)}{\sqrt{D(\lambda)^2 + u'^2}} \quad (6)$$

with $h_H(u)$ being the kernel of the Hilbert transform.

Thus, preferably the derivative of the cone-beam data is convoluted only in row-direction (that is in u-direction) with a kernel function, resulting in a Hilbert-like transform. The kernel $h_H(u)$ is preferably $1/\pi u$, as in the classical Hilbert transform, but one may also use a modified Hilbert filter with different apodization, or with a different bandwidth limitation. Therefore, the term Hilbert-like filter is used.

At some point after step A, the differentiation result is multiplied by a length-correction weight, also known as the cosine weight. In formula (6) above, this length-correction weight is written as $D(\lambda)/\sqrt{D(\lambda)^2 + u'^2}$.

In a next step C, the data is multiplied with a redundancy weighting function. Redundancy handling is necessary in order to take account of the fact that some ray paths through the object may be included twice in the data, i.e. if this particular path has been rayed from opposite sides.

According to a preferred embodiment, the redundancy waiting function is adapted to the particular trajectory. This allows the use of any possible trajectory, also non-convex trajectories. Thus, the waiting function is preferably calculated afresh for each trajectory. For non-convex trajectories, the redundancy waiting is not trivial, and it is not possible to resort to known functions such as the Parker waiting function. Only for convex trajectories, λ also has the meaning of a polar angle.

In practice, cone beam data contain few redundant data, since only rays in the plane of the trajectory can be redundant. However, in an embodiment the algorithm assumes that such pseudo-redundant rays actually contain the same information as an approximation.

For a circular trajectory, it is known to use a so-called Parker weighting function, which gives a contribution of 1 to each ray integral that is measured only once and balances the contributions of redundant data samples, using the property of the trigonometric functions, so that the weight corresponding to data samples considered twice for the reconstruction sum up to unity. The original Parker weighting function is disclosed in D. L. Parker "Optimal short scan convolution reconstruction for fan-beam CT" Med. Phys. 9 (2): 254-257, 1982.

For the present invention, it is preferred that similarly to the procedure used in the Feldkamp method, all points within a given filtered cone-beam projection that are located in the same column (i.e. that have the same u coordinate) receive the same weight, denoted as $w(\lambda,u)$.

According to an embodiment, the weight for a certain column is computed as follows: all complementary source points on the trajectory are identified, i.e. the points where the source trajectory intersects a plane perpendicular to the plane of the trajectory and parallel to the X-ray path at two points, namely at $a(\lambda)$ and through the detector column u. One then uses an auxiliary function $c(\lambda)$ and computes the redundancy weight as $$w(\lambda,u)=c(\lambda)/(c(\lambda)+c_c(\lambda,u)), \quad (7)$$

where $c_c(\lambda,u)$ is the sum of the auxiliary function evaluated at the source points that were determined to be complementary. The auxiliary function $c(\lambda)$ can in principal be any function which is pre-determined by the user, with the only limitations that $c \geq 0$ for all relevant λ. $c(\lambda)$ can for example be a constant, or can smoothly fall of at the edges. By the formula mentioned above, it is assured that all weights add up to 1. Preferably, by the above formula, a Parker-like redundancy weighting function can be achieved.

The function $w(\lambda,u)$ is preferably calculated new for each different trajectory, but one can always use the same auxiliary function.

The redundancy handling step C can either be performed after step B. In this case, the weighting function will be applied to the filtered cone-beam data. Alternatively, redundancy handling step C can be performed before step A. In this case, the weighting function will be multiplied with the original (acquired) cone-beam data.

The final reconstruction step D, the backprojection, will be performed after steps A-C, independent of their order. In step D, the filtered and redundancy weighted cone-beam data is backprojected into the image volume to compute a 3D image dataset $\hat{f}(\underline{x})$ which gives a good approximation of the object density $f(\underline{x})$. Preferably, the following formula is used for CB data that are non-truncated in u:

$$\hat{f}(\underline{x}) = \frac{1}{2\pi}\int_\Lambda d\lambda \frac{w(\lambda, u^*)}{R(\lambda) - \underline{x}\cdot \underline{e}_w(\lambda)} g_F(\lambda, u^*, v^*). \quad (8)$$

This equation describes a weighted backprojection of filtered CB data $g_F(\lambda,u,v)$ for all $\lambda \in \Lambda$, where $w(\lambda,u)$ is a Parker-like redundancy weighting function and where u* and v* are the detector coordinates of the projection of x for a given λ.

Preferably, a backprojection weight is used which is similar to that of the Feldkamp method but depends only on the distance, and not the square distance, between voxel and source point. Preferably, the backprojected values are accumulated in a 3D image dataset to successively compute the object density function, wherein for example one processed cone-beam projection after the other is used.

Since the reconstruction algorithm can handle non-circular trajectories, preferably the source trajectory is non-circular. In practice, this will not only encompass such deviations from a circular path as may happen in C-arm systems (for example within ±2 mm of a circular trajectory), but will imply a truly non-circular geometry. For example, the distance between the source and the detector may vary significantly, i.e. by >2 mm, preferably by >5 mm or >10 mm along the trajectory. Preferably, the variation will be smooth. Preferably, at least part of the source trajectory cannot be approximated by the segment of a circle.

The method of the invention is preferably applied to a geometry in which at least part of the source trajectory can be approximated by one or several straight lines. Such trajectory can for example be realized with an X-ray system where source and/or detector are mounted for translational movement, for example on rails and/or on telescopic aims. Alternatively, the trajectory is such that the tip of such telescopic arm moves in a straight line, preferably in its telescopic direction.

According to a preferred embodiment, the trajectory can be approximated by at least a part of a polygon, for example a polygon made up of 3 to 10 straight lines spanning a polar angle Λ of 180° to 360°, preferably 200° to 300°.

The detector preferably moves along a corresponding path opposite to the X-ray source, such that cone-beam projections from the object can be acquired at each point along the source trajectory, with as little truncation as possible. However, the reconstruction method can even handle truncated data, for example when data extrapolation methods are used to estimate the projection data beyond the detector boundaries. One possible extrapolation method is to let the data values fall off smoothly beyond the detector boundaries.

Alternatively, the detector may also stay at the same position during an acquisition of a series of cone-beam projection.

The present invention is usable for cases where the whole object is comprised inside the field of view, or where the object to be examined is part of a larger object not completely contained within the field of view. In the last case, it may be possible to extrapolate the areas outside the field of view for example by a smooth fall-off of the cone-beam projection data $g(\lambda,u,v)$.

The invention is also directed to an imaging system capable of producing a 3D image dataset of an object to be imaged, comprising an X-ray source and a detector, which preferably are adapted to move along trajectories described above.

The imaging system further comprises an acquisition system for acquiring a series of two-dimensional arrays of cone-beam data while the source moves along the trajectory around the object. Thus, the acquisition may for example comprise mountings for the X-ray source and the detector, allowing them to move around the object, for example on rails or telescopic arms. Further, the acquisition system may comprise a control unit controlling the movement of source and detector.

Further, the imaging system comprises an image reconstruction system which is adapted for reconstructing a 3D image from the cone beam data according to the method described above. The image reconstruction system can be implemented on a computer, for example a PC or workstation including a CPU and working memory (e.g. RAM).

Alternatively, the imaging system may be a robot-based C-arm system or any other X-ray system where the distance between source and detector may vary for different projection angles.

One application of the invention is medical imaging. However, it may also be applied in an industrial context, in particular to non destructive testing (for example of workpieces of metal or other materials) and other applications.

The invention is finally directed to a computer program product containing computer-readable software code portions adapted to cause a computer to perform the following steps when the program is run on a computer: accessing a series of two-dimensional arrays of cone-beam data acquired by a detector comprising a two-dimensional array of detector elements, while an X-ray emitting photon rays in a cone-beam moved along a substantially planar trajectory around an object to be imaged, the trajectory being described by a series of points in space serially numbered by a counter parameter; and reconstructing a 3D image from the cone-beam data by the method described above. Preferably, the computer program product is directly loadable into the internal memory of a digital computer. The invention is also directed to the computer program per se, and to a computer usable medium or digitally readable medium, on which such computer program is stored.

BRIEF DESCRIPTION OF THE DRAWINGS

The invention will now be described further by means of preferred embodiments with reference to the attached drawings, in which.

DETAILED DESCRIPTION OF THE INVENTION

Figure 1:
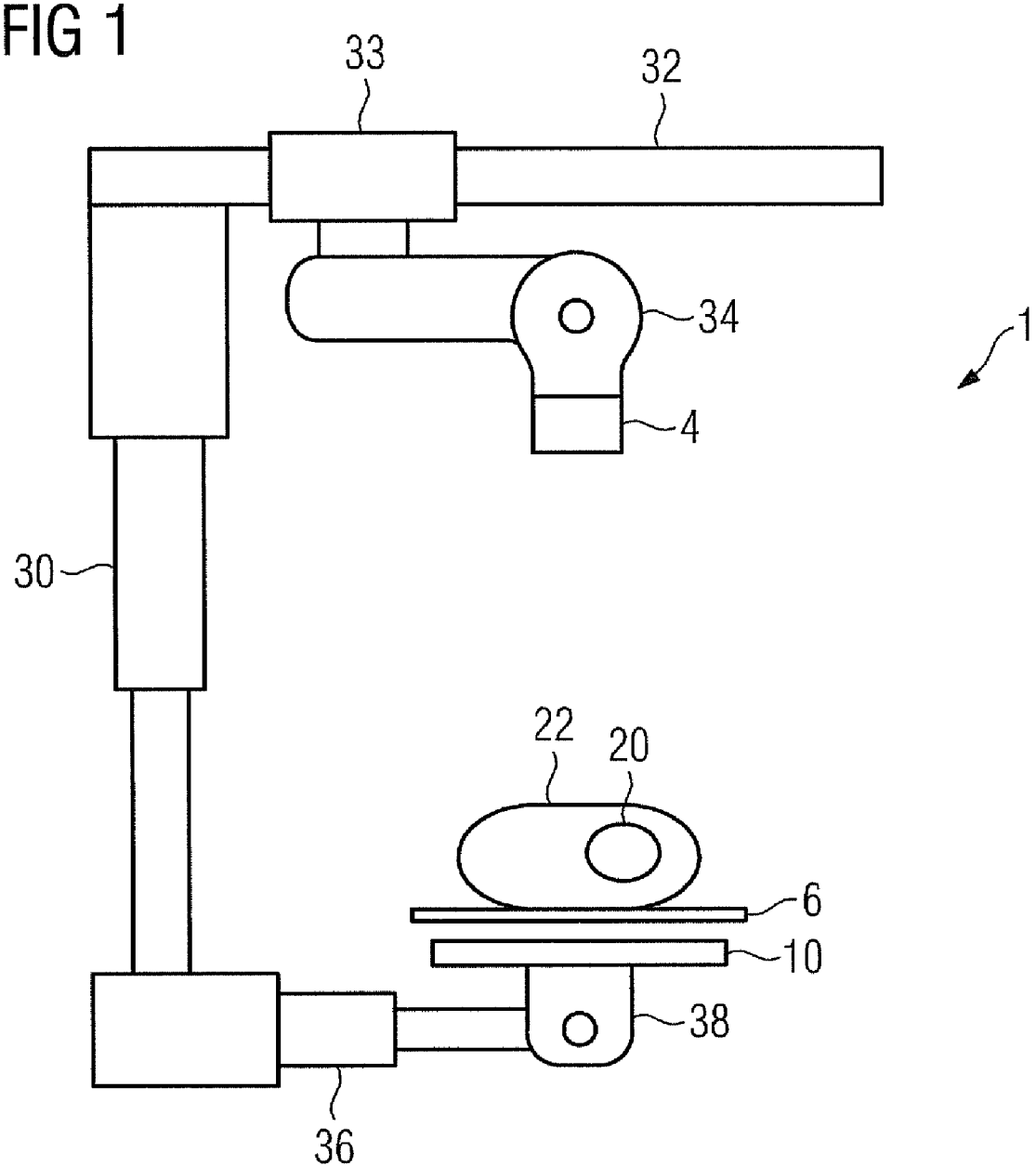
FIG. 1 is a schematic representation of an imaging system on which the present invention may be implemented.

FIG. 1 is a schematic illustration of an X-ray imaging system on which the present invention may be implemented.

A patient 22 may be placed on a patient bed 6. The object to be imaged may be an area 20 within the patient. An X-ray source 4 is mounted to be translationally movable in several directions by means of telescope arm 30 and rail 32, along which the X-ray source may slide at slider 33. In addition, the X-ray source is pivotably mounted on joint 34, so that it may be tilted such that its emitted cone-beam of X-rays will go through the object 20 and afterwards hit the detector 10.

The detector 10 is preferably a flat-panel detector and is itself tiltably mounted through joint 38. The joint 38 can be translationally moved on telescopic arm 36.

It should be noted that infinite variations are possible concerning the construction of the imaging system, in particular as regards the mounting of the X-ray source 4 and the detector 10. For example, the source 4 may be mounted on rails, possibly with telescopic aims, on the ceiling of the room. Further, configurations are possible where only the source moves along telescopic arms, whereas the detector tilts around the object. Preferably, source and/or detector are each movable in at least two directions or have at least two, preferably three or four degrees of freedom.

The telescopic arms 30,36 can be moved hydraulically, or by electrical motors.

Figure 2:
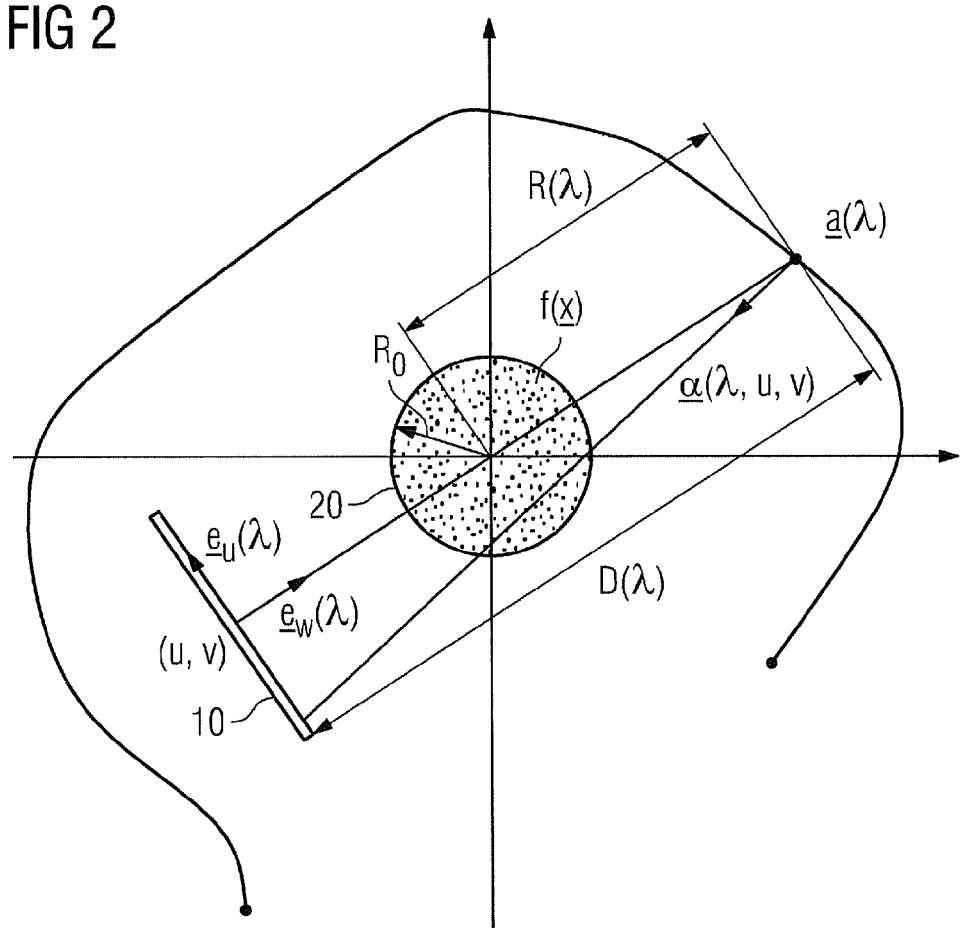
FIG. 2 is a top-view illustration of a variable-radius trajectory and object.

FIG. 2 is a schematic illustration of the variable radius geometry, wherein the trajectory $a(\lambda)$ is lying in the plane of the paper, and the detector 10 is perpendicular thereto. The object 20 to be imaged is situated around the origin of the coordinate system.

Figure 3:
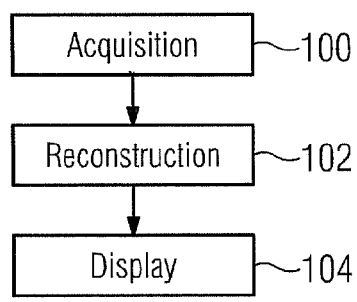
FIG. 3 is a flow-diagram of an embodiment of the inventive method.

FIG. 3 is a flow diagram showing the main steps of an embodiment of the method. In step 100, a series of cone-beam projections are acquired in a scan, wherein the X-ray source moves along a planar variable-radius trajectory around the object. In one scan, typically from about 50-300, preferably 150-250 cone-beam projections will be acquired.

In step 102, which itself comprises steps A-D, the cone-beam data acquired in step 100 are reconstructed to a 3D image dataset. Optionally, such image can be displayed on a screen or printed on paper in step 104, so the image dataset can be viewed and possibly further processed. As is known in the art, such 3D image dataset may be used to correlate 3D data with real-time 2D projections acquired on the same imaging systems during a later stage of the session, for example in order to control an intervention.

Figure 4:
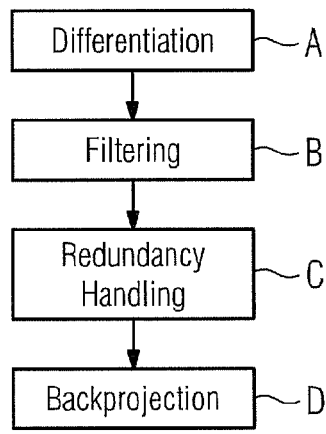
FIG. 4 is a flow-diagram of a first embodiment of the reconstruction method.

FIG. 4 shows a first embodiment of the reconstruction method consisting of a differentiation of the cone-beam data in step A, filtering preferably with a Hilbert-filter and multiplication with a length-correction weight in step B. The result of step B is multiplied with a redundancy weighting function in step C. Finally, in step D the processed cone-beam data are back-projected into the 3D volume to produce a 3D image dataset.

Figure 5:
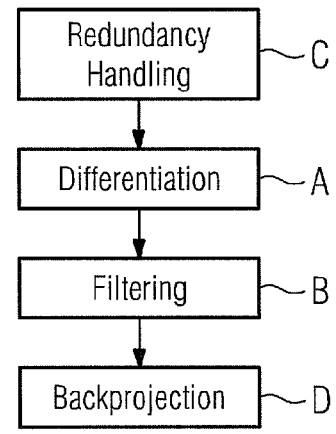
FIG. 5 is a flow-diagram of a second embodiment of the reconstruction method.

According to the second embodiment of FIG. 5, step C, namely the redundancy handling, may also be performed first, followed by differentiation in step A, filtering in step B and backprojection in step D.

EXAMPLE

Figure 6:
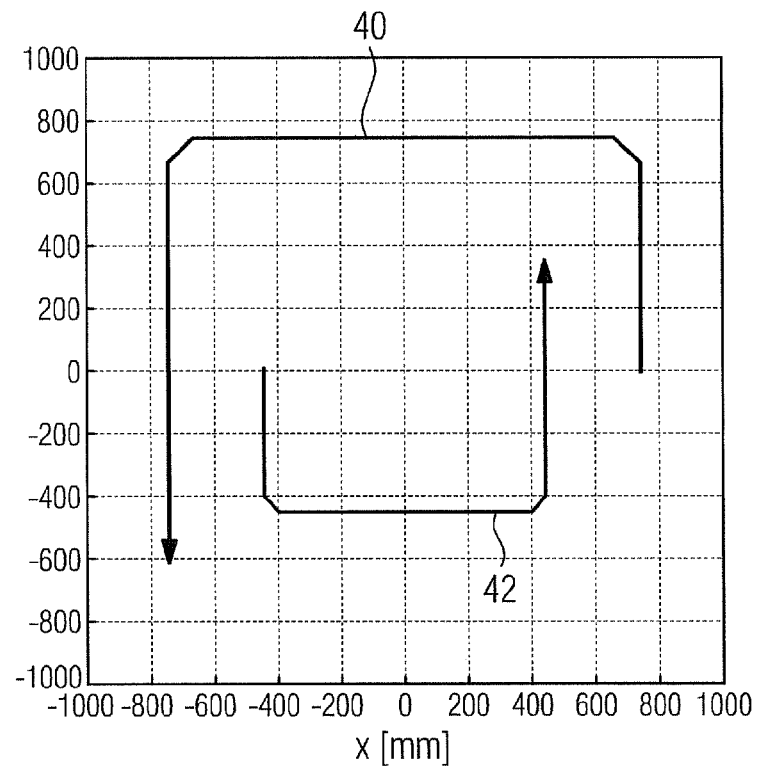
FIG. 6-8 slices z=0 mm, z=80 mm and x=5 mm through the head phantom reconstructions in [0,100] Houndsfield units (HU)
Figure 7:
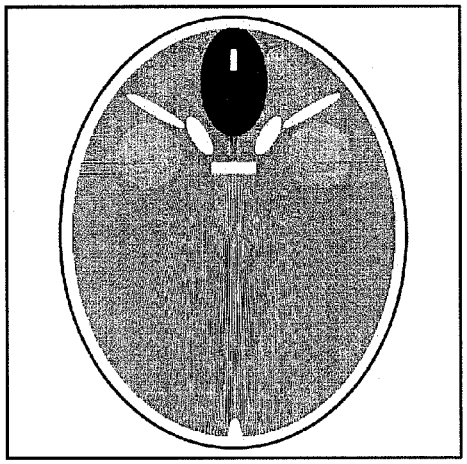

The inventive method was tested in an approximately rectangular short-scan geometry as shown in FIG. 6. The trajectory of the X-ray source during the scan is indicated at 40, and the trajectory of the detector at 42. Each moves along roughly a rectangular trajectory, wherein the edges are leveled.

In this geometry, trajectory radius and the source-detector distance where parameterized as $$R(\lambda) = R_m 1(\lambda) \text{ and } D(\lambda) = D_m 1(\lambda)$$

where $R_m=750$ mm and $D_m=1200$ mm were the minimum radius and the minimum source-detector distance, respectively, and where $$l(\lambda)=\min(|\cos\lambda|^{-1};|\sin\lambda|^{-1};\sqrt{2}-\epsilon) \quad (9)$$

is a scaling function that modulates the geometry. The scalar $\epsilon$ in this definition was used to avoid the 90°-edges in the trajectory and was set to 0.07 in our evaluation, yielding the trajectory of FIG. 6.

CB projections of the FORBILD head phantom were simulated over the interval $\lambda=[0°, 220°]$, using a constant increment $\Delta\lambda=0.5°$ and assuming detector dimensions $U_m=20$ mm and $U_m=15$ cm and square pixels of size 0.5 mm. Reconstruction was carried out using a smooth Parker-like redundancy weighting function $w(\lambda,u)$.

Figure 10:
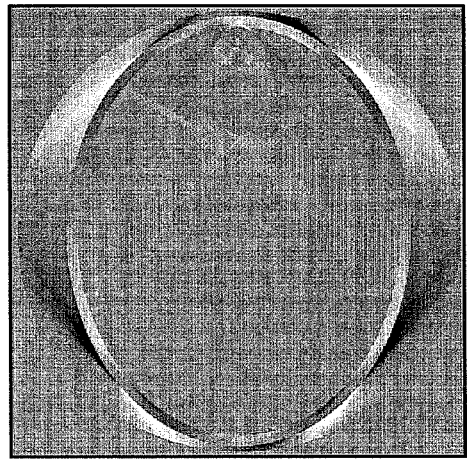
FIG. 9-11 contribution of the new term to the final reconstruction at slices z=0 mm, z=80 mm and x=5 mm in a window of width 100 on the HU-scale.
Figure 8:
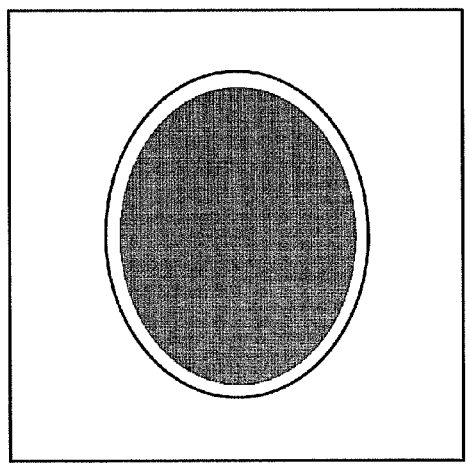
Figure 11:
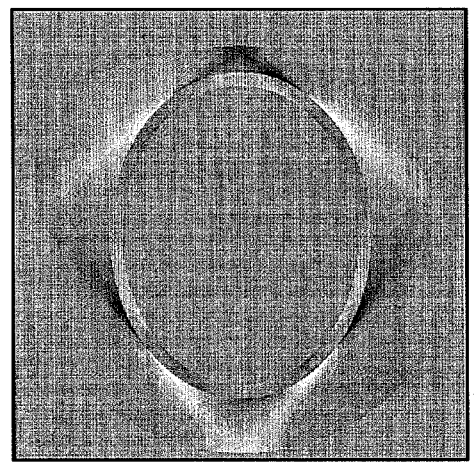
Figure 9:
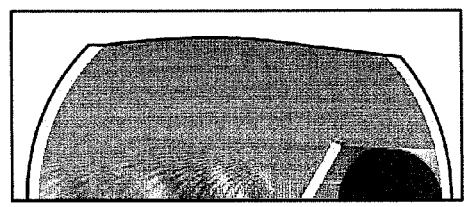
Figure 12:
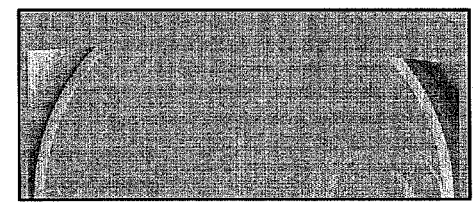
FIG. 12 illustration of the exemplary trajectories of the X-ray source and the detector center during the scan in a short-scan rectangular geometry.

The results are presented in FIGS. 7-12. These figures present two axial and one coronal slice through the reconstruction results, wherein areas outside the field of view are shown as black (left hand side) or gray (right hand side). As is visible especially in FIG. 7, the slice at z=0 mm, a good reconstruction of the FORBILD head phantom was possible. FIGS. 10-12 show the contribution associated with the NEW TERM mentioned above, which appears to correct for gradients in the reconstruction results.

The present invention provides for a practical Feldkamp-like reconstruction method for flat-panel cone-beam reconstruction from a planar source trajectory, in particular with smoothly varying radius. Along with the reconstruction, the method also recovers the field-of-view, which can take complex shapes in the considered geometries.

The invention claimed is:

1. A method for reconstructing a 3D image dataset of an object with an imaging system having an X-ray source and an x-ray detector, comprising:
    acquiring a series of two-dimensional arrays of cone beam data from the x-ray detector while the x-ray source moves along a variable radius, non-circular path having a planar trajectory around the object, the trajectory being described by a series of source points along the non-circular path serially numbered by a counter parameter;
    differentiating the acquired cone beam data with respect to the counter parameter of the planar trajectory at a fixed x-ray ray direction to produce a derivative of the cone beam data;
    filtering the derivative with a Hilbert-like filter to produce a filtered cone beam data;
    multiplying the acquired cone beam data with a redundancy weighting function before the differentiating step or multiplying the filtered cone beam data with the redundancy weighting function after the filtering step to produce a processed cone beam data; and
    back-projecting the processed cone beam data for reconstructing the 3D image dataset.

2. The method as claimed in claim 1, wherein a distance between the x-ray source and the x-ray detector varies along the trajectory.

3. The method as claimed in claim 1, wherein at least part of the trajectory has a shape of a polygon approximated by a finite number of straight lines.

4. The method as claimed in claim 3, wherein the number of the straight lines comprises 1 to 30 straight lines.

5. The method as claimed in claim 1, wherein the trajectory is non-convex.

6. The method as claimed in claim 1, wherein the derivative is filtered only in a direction parallel to a plane of the trajectory.

7. The method as claimed in claim 1, wherein the redundancy weighting function is adapted to the trajectory.

8. The method as claimed in claim 1, wherein the redundancy weighting function is defined by:
    identifying complementary source points on the trajectory;
    accessing an auxiliary function $c(\lambda)$ defined for all source points along the trajectory; and
    computing the redundancy weighting function as:

$$w(\lambda,u)=c(\lambda)/(c(\lambda)+c_c(\lambda,u)),$$

wherein
    $\lambda$ is the counter parameter,
    w is the redundancy weighting function,
    $c_c(\lambda,u)$ is a sum of the auxiliary function evaluated at the complementary source points.

9. The method as claimed in claim 1, wherein the processed cone beam data is back-projected by a weight that is inversely proportional to a distance between a source point and a position of a currently computed voxel within the 3D image dataset.

10. An imaging system for producing a 3D image dataset of an object, comprising:
    an x-ray source for emitting photon rays in a cone beam;
    an x-ray detector comprising a two-dimensional array of detector elements for acquiring a series of two-dimensional arrays of cone beam data while the x-ray source moves along a variable radius, non-circular path having a planar trajectory around the object, the trajectory being described by a series of source points along the non-circular path serially numbered by a counter parameter; and
    an image reconstruction system for reconstructing the 3D image dataset by:
        differentiating the acquired cone beam data with respect to the counter parameter of the trajectory at a fixed x-ray ray direction to produce a derivative of the cone beam data;
        filtering the derivative with a Hilbert-like filter to produce a filtered cone beam data;
        multiplying the acquired cone beam data with a redundancy weighting function before the differentiating step or multiplying the filtered cone beam data with the redundancy weighting function after the filtering step to produce a processed cone beam data; and
        back-projecting the processed cone beam data for reconstructing the 3D image dataset.

11. The imaging system as claimed in claim 10, wherein the X-ray source and the x-ray detector are mounted on separate telescopic arms.

12. The imaging system as claimed in claim 10, wherein the trajectory is a non-circular trajectory.

13. The imaging system as claimed in claim 12, wherein part of the trajectory is approximated by a polygon.

14. A computer program stored on a non-transitory computer readable medium for producing a 3D image dataset of an object, wherein, when executed on the computer, the program performs the following steps comprising:
    accessing a series of two-dimensional arrays of cone beam data acquired by an x-ray detector while an x-ray source moves along a variable radius, non-circular path having a planar trajectory around the object, the trajectory being described by a series of source points along the non-circular path serially numbered by a counter parameter;

differentiating the acquired cone beam data with respect to the counter parameter of the trajectory at a fixed x-ray ray direction to produce a derivative of the cone beam data;
filtering the derivative with a Hilbert-like filter to produce a filtered cone beam data;
multiplying the acquired cone beam data with a redundancy weighting function before the differentiating step or multiplying the filtered cone beam data with the redundancy weighting function after the filtering step to produce a processed cone beam data; and
back-projecting the processed cone beam data for reconstructing the 3D image dataset.

* * * * *